US011617537B2

(12) United States Patent
Sarrafzadeh et al.

(10) Patent No.: US 11,617,537 B2
(45) Date of Patent: Apr. 4, 2023

(54) FABRIC-BASED PRESSURE SENSOR ARRAYS INCLUDING INTERSECTING ELONGATED CONDUCTIVE STRIPS ON OPPOSITE SIDES OF A TEXTILE SHEET

(71) Applicants: The Regents of the University of California, Oakland, CA (US); Medisens Wireless, Inc., Santa Clara, CA (US)

(72) Inventors: Majid Sarrafzadeh, Anaheim Hills, CA (US); Wenyao Xu, Los Angeles, CA (US); Ming-Chun Huang, Culver City, CA (US); Nitin Raut, Sunnyvale, CA (US); Behrooz Yadegar, Los Altos, CA (US)

(73) Assignees: The Regent of the University of California, Oakland, CA (US); Medisens Wireless, Inc., Santa Clara, CA (US)

( * ) Notice: Subject to any disclaimer, the term of this patent is extended or adjusted under 35 U.S.C. 154(b) by 0 days.

(21) Appl. No.: 15/002,136

(22) Filed: Jan. 20, 2016

(65) Prior Publication Data
US 2016/0135744 A1    May 19, 2016

Related U.S. Application Data

(63) Continuation of application No. 13/475,654, filed on May 18, 2012, now Pat. No. 9,271,665.
(Continued)

(51) Int. Cl.
*G01L 1/18* (2006.01)
*A61B 5/00* (2006.01)
(Continued)

(52) U.S. Cl.
CPC .......... *A61B 5/6804* (2013.01); *A61B 5/1116* (2013.01); *A61B 5/4561* (2013.01);
(Continued)

(58) Field of Classification Search
CPC ................ A61B 5/6829; A61B 5/6804; A61B 2562/046; A61B 2562/0247; G01L 1/146; G01L 1/205
See application file for complete search history.

(56) References Cited

U.S. PATENT DOCUMENTS 3,996,922 A    12/1976 Basham
4,359,726 A    11/1982 Lewiner et al.
(Continued)

OTHER PUBLICATIONS

Electrically Conducting Yarn, http://en.wikipedia.org/wiki/Electrically_Conducting_yarn, accessed on Apr. 1, 2015.
(Continued)

*Primary Examiner* — Tran M. Tran
(74) *Attorney, Agent, or Firm* — Foley & Lardner LLP

(57) ABSTRACT

A fabric-based pressure sensor array includes: (1) a first layer including M elongated conductive strips coated thereon; (2) a second layer including N elongated conductive strips coated thereon, the M elongated conductive strips extending crosswise relative to the N elongated conductive strips to define M×N intersections; and (3) a unitary textile sheet extending between the first layer and the second layer so as to overlap the M×N intersections, the textile sheet having a variable resistivity in response to applied pressure so as to define M×N pressure sensors at locations corresponding to the M×N intersections.

13 Claims, 11 Drawing Sheets

Top view

Bottom view

Related U.S. Application Data

(60) Provisional application No. 61/488,653, filed on May 20, 2011.

(51) Int. Cl.
  *G01L 1/20* (2006.01)
  *A61B 5/11* (2006.01)

(52) U.S. Cl.
  CPC .............. *A61B 5/7278* (2013.01); *G01L 1/18* (2013.01); *G01L 1/205* (2013.01); *A61B 5/4806* (2013.01); *A61B 2562/0247* (2013.01); *A61B 2562/046* (2013.01)

(56) References Cited

U.S. PATENT DOCUMENTS

| | | | |
|---|---|---|---|
| 4,509,527 A | 4/1985 | Fraden | |
| 4,644,801 A * | 2/1987 | Kustanovich | G01L 1/146 361/283.1 |
| 4,827,763 A | 5/1989 | Bourland et al. | |
| 5,033,291 A * | 7/1991 | Podoloff | A61B 5/1036 73/172 |
| 5,079,949 A | 1/1992 | Tamori | |
| 5,234,065 A | 8/1993 | Schmidt | |
| 5,372,365 A * | 12/1994 | McTeigue | A63B 24/0003 434/252 |
| 5,799,533 A * | 9/1998 | Seki | A61B 5/1036 338/99 |
| 6,155,120 A † | 12/2000 | Taylor | |
| 6,194,537 B1 | 2/2001 | Raue et al. | |
| 6,216,545 B1 | 4/2001 | Taylor | |
| 6,280,392 B1 * | 8/2001 | Yoshimi | A61B 5/7415 600/534 |
| 6,333,736 B1 | 12/2001 | Sandbach | G06F 3/0414 178/18.03 |
| 6,369,804 B1 * | 4/2002 | Sandbach | G01L 1/205 178/18.05 |
| 6,413,634 B1 | 7/2002 | Tanaka et al. | |
| 6,452,479 B1 * | 9/2002 | Sandbach | G06F 3/045 338/101 |
| 6,485,441 B2 * | 11/2002 | Woodward | A61B 5/6892 600/595 |
| 6,543,299 B2 | 4/2003 | Taylor | |
| 6,646,540 B1 * | 11/2003 | Lussey | H01C 10/106 338/114 |
| 6,826,968 B2 * | 12/2004 | Manaresi | B63H 9/06 73/862.046 |
| 7,145,432 B2 | 12/2006 | Lussey et al. | |
| 7,161,084 B2 | 1/2007 | Sandbach | |
| 7,217,244 B2 | 5/2007 | Suzuki et al. | |
| 7,301,351 B2 | 11/2007 | Deangelis et al. | |
| 7,301,435 B2 | 11/2007 | Lussey et al. | |
| 7,365,031 B2 | 4/2008 | Swallow et al. | |
| 7,388,507 B2 | 6/2008 | Bader | |
| 7,463,040 B2 * | 12/2008 | Qi | H01B 1/124 324/693 |
| 7,515,059 B2 | 4/2009 | Price et al. | |
| 7,544,627 B2 * | 6/2009 | Tao | D03D 1/0088 442/189 |
| 7,591,165 B2 * | 9/2009 | Papakostas | G01L 1/205 324/616 |
| 7,657,956 B2 | 2/2010 | Stacy et al. | |
| 7,683,643 B2 * | 3/2010 | Qi | H01B 1/124 324/693 |
| 7,770,473 B2 * | 8/2010 | Von Lilienfeld-Toal | A61B 5/1036 73/862.68 |
| 7,824,769 B2 | 11/2010 | Nakatsuka et al. | |
| 7,984,544 B2 | 7/2011 | Rosenberg | |
| 8,031,080 B2 | 10/2011 | Price et al. | |
| 8,089,336 B2 * | 1/2012 | Burkitt | G06F 3/0202 338/101 |
| 8,107,153 B2 * | 1/2012 | Sotzing | G02F 1/1533 359/265 |
| 8,161,826 B1 † | 4/2012 | Taylor | |
| 8,253,696 B2 * | 8/2012 | Antaki | G06K 9/0002 178/18.06 |
| 8,479,585 B2 * | 7/2013 | Shaw-Klein | H01L 41/081 73/777 |
| 8,598,893 B2 | 12/2013 | Camus | |
| 8,672,842 B2 | 3/2014 | Kenalty et al. | |
| 8,710,823 B2 | 4/2014 | Tsukada et al. | |
| 8,884,913 B2 | 11/2014 | Saynac et al. | |
| 8,904,876 B2 | 12/2014 | Taylor et al. | |
| 8,948,839 B1 * | 2/2015 | Longinotti-Buitoni | A61B 5/7405 600/382 |
| 8,966,997 B2 | 3/2015 | Taylor | |
| 9,057,653 B2 * | 6/2015 | Schediwy | G01L 1/146 |
| 9,107,586 B2 * | 8/2015 | Tran | A61B 5/7271 |
| 9,125,625 B2 * | 9/2015 | Wang | A61B 5/1477 |
| 9,182,750 B2 * | 11/2015 | Rawls-Meehan | A47C 31/008 |
| 9,733,136 B2 * | 8/2017 | Seitz | A61B 5/00 |
| 10,864,137 B2 * | 12/2020 | Rawls-Meehan | A47C 20/041 |
| 2005/0124864 A1 | 6/2005 | Mack et al. | |
| 2005/0268962 A1 | 12/2005 | Gaudiana et al. | |
| 2006/0267321 A1 | 11/2006 | Harish et al. | |
| 2007/0202765 A1 * | 8/2007 | Krans | G06F 3/0414 442/301 |
| 2008/0050550 A1 * | 2/2008 | Orth | G06F 3/044 428/90 |
| 2008/0093687 A1 * | 4/2008 | Antaki | G06K 9/0002 257/415 |
| 2008/0200085 A1 * | 8/2008 | Van Bruggen | G06F 3/0412 442/117 |
| 2010/0021637 A1 * | 1/2010 | Revol Cavalier | D06M 13/513 427/258 |
| 2010/0308846 A1 | 12/2010 | Camus | |
| 2012/0116251 A1 | 5/2012 | Ben-Shalom et al. | |
| 2012/0152260 A1 * | 6/2012 | Flinsenberg | A61F 5/56 128/848 |
| 2012/0277637 A1 * | 11/2012 | Vahdatpour | A47C 31/123 600/595 |
| 2012/0323501 A1 | 12/2012 | Sarrafzadeh et al. | |
| 2013/0281815 A1 | 10/2013 | Varadan | |
| 2014/0373594 A1 * | 12/2014 | Remez | G01L 25/00 73/1.08 |
| 2015/0168238 A1 * | 6/2015 | Raut | G01N 27/223 702/42 |

OTHER PUBLICATIONS

Keogh et al. (2006), "Lb keogh supports exact indexing of shapes under rotation invariance with arbitrary representations and distance measures", ACM International Conference on Very Large Data Bases, pp. 56-78.

U.S. Final Office Action dated Jul. 30, 2015 for U.S. Appl. No. 13/475,654.

U.S. Non-Final Office Action dated Apr. 17, 2015 for U.S. Appl. No. 13/475,654.

U.S. Notice of Allowance dated Oct. 26, 2015 for U.S. Appl. No. 13/475,654.

U.S. Restriction Requirement dated Jan. 26, 2015 for U.S. Appl. No. 13/475,654.

Xu et al., eCushion: an eTextile device for sitting posture monitoring, 2011, Int'l Conf on body Sensor Networks.

\* cited by examiner
† cited by third party (a) Textile Sensor Array (b) Arduino + Bluetooth (c) Smart Phone (a) Map One  (b) Map Two (a) Four Fingers (b) Finger Image with crosstalk (c) Finger Image without crosstalk

FABRIC-BASED PRESSURE SENSOR ARRAYS INCLUDING INTERSECTING ELONGATED CONDUCTIVE STRIPS ON OPPOSITE SIDES OF A TEXTILE SHEET

CROSS-REFERENCE TO RELATED APPLICATIONS

This application is a continuation of U.S. patent application Ser. No. 13/475,654, filed May 18, 2012, which claims the benefit under Section 119(e) from U.S. Provisional Application No. 61/488,653 filed May 20, 2011, the disclosure of each of which is incorporated herein by reference in its entirety.

FIELD OF THE INVENTION

The invention generally relates to pressure sensors and, more particularly, to fabric-based pressure sensor arrays.

BACKGROUND

Sitting is one of the most common positions of human beings. As reported by public media, people will typically sit about six hours per day in their daily lives, and specific sitting positions are related to a number of health issues, such as back pain. Sitting position monitoring is receiving increasingly more attention due to its extensive applications and large impact in a number of domains, such as biomedicine (e.g., rehabilitation evaluation in chronic diseases), health education (e.g., correct sitting position for back pain prevention), human computer interface (e.g., real-time sitting position analysis for gaming), and facility design (e.g., furniture fitness evaluation).

Sleeping is another one of the most common positions of human beings, with people spending about seven or eight hours sleeping on average in their daily lives. Pressure ulcers have become a serious problem for paralyzed and other mobility-impaired patients, who tend to spend increased time in bed and can be affected by skin breakdown. An efficient approach to prevent ulcers is to make patients comfortable by changing their sleeping positions frequently. To achieve this goal, it is desirable to monitor sleeping positions of the patients, and alert nurses or other healthcare practitioners to change their sleeping positions in a timely fashion.

In order to monitor sitting or sleeping position accurately and reliably, attempts have been made to use sensors to extract posture information. Intuitively, it might be expected that a camera is a straightforward way to extract posture information by image capture. However, a camera can render patients uncomfortable because it can record other information that impacts personal privacy, especially when the patients are sleeping. Compared to a camera, a pressure sensor is more economical and more readily deployed. However, pressure sensors are commonly manufactured from piezoelectric crystals or ceramics, such as quartz, which can be obtrusive and uncomfortable for daily use.

It is against this background that a need arose to develop the apparatus, system, and method described herein.

SUMMARY

One aspect of the invention relates to a fabric-based pressure sensor array. In one embodiment, the sensor array includes: (1) a first layer including M elongated conductive strips coated thereon; (2) a second layer including N elongated conductive strips coated thereon, the M elongated conductive strips extending crosswise relative to the N elongated conductive strips to define M×N intersections; and (3) a unitary textile sheet extending between the first layer and the second layer so as to overlap the M×N intersections, the textile sheet having a variable resistivity in response to applied pressure so as to define M×N pressure sensors at locations corresponding to the M×N intersections.

In another embodiment, the sensor array includes a textile sheet having a first surface and a second surface, and including M elongated conductive strips coated on the first surface and N elongated conductive strips coated on the second surface. The M elongated conductive strips extend crosswise relative to the N elongated conductive strips to define M×N intersections, and the textile sheet has a variable resistivity in response to applied pressure so as to define M×N pressure sensors at locations corresponding to the M×N intersections.

In another embodiment, the sensor array includes: (1) a textile sheet having a first surface and a second surface; (2) a plurality of contact pads disposed adjacent to the first surface of the textile sheet; and (3) a ground contact pad disposed adjacent to the second surface of the textile sheet and sized so as to at least partially overlap each of the plurality of contact pads to define a plurality of overlapping regions. The textile sheet exhibits piezoresistivity so as to define a plurality of pressure sensors at locations corresponding to the plurality of overlapping regions.

Another aspect of the invention relates to a non-transitory computer-readable storage medium. In one embodiment, the storage medium includes executable instructions to: (1) receive a pressure distribution of an object as applied against an array of pressure sensors; (2) select a pressure value from the pressure distribution as an outlier pressure value; (3) adjust the outlier pressure value according to neighboring pressure values in the pressure distribution to derive an updated pressure distribution; and (4) based on the updated pressure distribution, derive a posture of the object as applied against the array of pressure sensors.

In another embodiment, the storage medium includes executable instructions to: (1) receive a pressure map of a human subject as applied against an array of pressure sensors, at least a subset of the array of pressure sensors being coupled via crosstalk; (2) apply a decoupling transformation to the pressure map to derive an updated pressure map in which crosstalk is at least partially reduced; and (3) based on the updated pressure map, derive a posture of the human subject as applied against the array of pressure sensors.

Another aspect of the invention relates to a system for posture recognition. In one embodiment, the system includes: (1) a processing unit; and (2) a memory connected to the processing unit and including executable instructions to: (a) receive data corresponding to a two-dimensional pressure distribution of an object as applied against a sensor sheet; (b) convert the data into an one-dimensional pressure sequence; and (c) based on the pressure sequence, infer a posture of the object as applied against the sensor sheet.

Other aspects and embodiments of the invention are also contemplated. The foregoing summary and the following detailed description are not meant to restrict the invention to any particular embodiment but are merely meant to describe some embodiments of the invention.

BRIEF DESCRIPTION OF THE DRAWINGS

For a better understanding of the nature and objects of some embodiments of the invention, reference should be made to the following detailed description taken in conjunction with the accompanying drawings.

DETAILED DESCRIPTION

Embodiments of the invention are directed to fabric-based (or textile) pressure sensors for recognition of bodily postures, such as postures of a human body or postures of part of a human body. Through the use of a fabric-based pressure sensor array, embodiments can extract or infer a three-dimensional posture of an object based on a two-dimensional distribution of weight of the object as applied against the sensor array. In order to compensate for certain variability or uncertainty factors that are characteristic of fabric-based pressure sensors, efficient procedures are implemented to mitigate against their influence and provide high recognition accuracy for monitoring purposes. For example, a sitting position or a sleeping position can be accurately extracted from a two-dimensional pressure map resulting from a user sitting or lying on the sensor array. As another example, a gait can be accurately extracted from a sequence of two-dimensional pressure maps resulting from the application of force or pressure against the sensor array as a user walks.

The use of fabric-based pressure sensors provides a number of advantages over conventional pressure sensors. For example, fabric-based pressure sensors can closely approximate a feel, a thickness, or a weight of conventional fabrics and, therefore, can be unobtrusively incorporated in a number of textile products that are comfortable for daily use. Examples of textile products that can benefit from the incorporation of fabric-based pressure sensors include apparel (e.g., clothing, drysuits, and protective suits), footwear (e.g., socks, shoes, and shoe insoles), medical products (e.g., thermal blankets and hospital bed sheets), household products (e.g., bed sheets, mattresses, seat cushions, pillows, pillow cases, and carpets), transportation products (e.g., car seats and bicycle seats), outdoor products (e.g., sleeping bags), and other products that are wearable or otherwise subject to applied force or pressure from a human body or part of a human body. Also, a resolution, a size, and a shape of a fabric-based pressure sensor array can be readily scaled or tailored for any specific application. Examples of applications that can benefit from the use of fabric-based pressure sensors include sitting position monitoring for back pain prevention, sleeping position monitoring for ulcer prevention, real-time sitting position analysis for gaming, sitting or sleeping position monitoring for furniture fitness evaluation, gait analysis for back pain prevention, and sitting position monitoring for activating or otherwise controlling air bags.

Fabric-Based Pressure Sensor System

Figure 1:
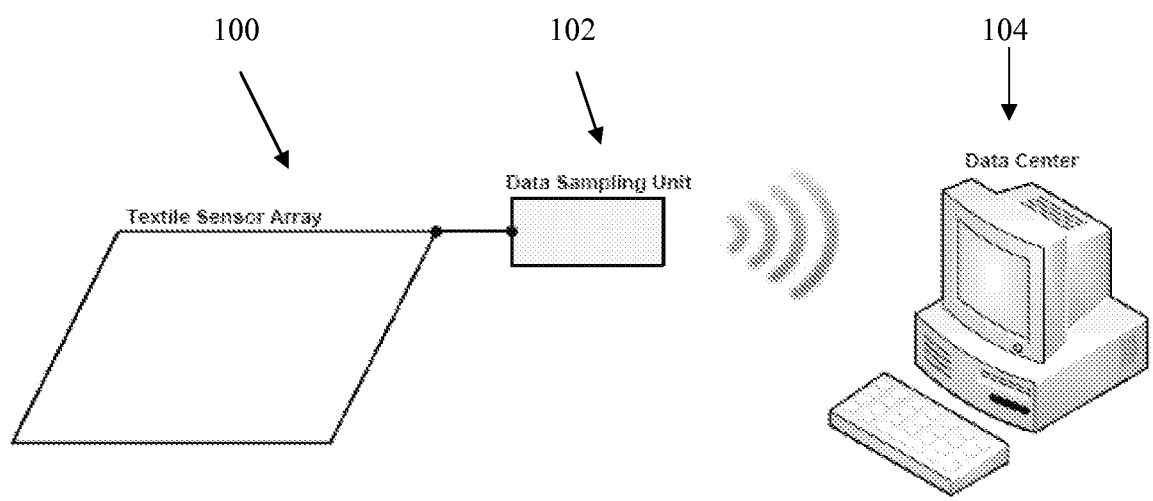
FIG. 1: Architecture of a fabric-based pressure sensor system for posture recognition, according to an embodiment of the invention.

FIG. 1 shows an architecture of a fabric-based pressure sensor system, according to an embodiment of the invention. The system can be implemented for health status monitoring in a clinical setting of a hospital or for daily use at a home or an office, where a user can be remotely monitored. Accordingly, the system is desirably implemented for convenience of access, straightforward deployment, and unobtrusiveness during use. Also, the system can be implemented with relatively low-cost and can be seamlessly compatible with existing computer systems found in hospitals, homes, and office buildings.

Referring to FIG. 1, the system includes three main components: a textile sensor array 100, a data sampling unit 102, and a data center 104. The textile sensor array 100 captures a two-dimensional pressure distribution of a user as the user lies on, sits on, or otherwise applies force or pressure on the texture sensor array 100, and the data sampling unit 102 acquires sensor outputs corresponding to the pressure distribution and conveys the sensor outputs to the data center 104 via wireless or wired transmission.

The data center 104 processes the sensor outputs for health status monitoring or other applications. Specifically, the data center 104 executes or otherwise performs calibration and posture recognition procedures described in the following sections to recognize a posture of the user. In the case of health status monitoring, the data center 104 can recognize recurring a sleeping position or different sleeping positions with common pressure areas, and can generate alerts for a nurse or another healthcare practitioner to change the sleeping position of the user. In the case of sitting position monitoring, the data center 104 can recognize different sitting positions based on a pressure distribution across sensors within the textile sensor array 10. For example, when the user is in a "forward" sitting position, the user can apply greater pressure towards a front side of the textile sensor array 100, and, when the user is in a "backward" sitting position, the user can apply greater pressure towards a back side of the textile sensor array 100. As another example, when the user is in a "left lean" sitting position, the user can apply greater pressure towards a left side of the textile sensor array 100, and, when the user is in a "right lean" sitting position, the user can apply greater pressure towards a right side of the textile sensor array 100.

Although the textile sensor array 100, the data sampling unit 102, and the data center 104 are shown as separate components in FIG. 1, it is contemplated that these components can be combined or further sub-divided in other embodiments. It is also contemplated that processing performed by the data center 104 also can be performed in whole or in part by another component, such as the data sampling unit 102.

Figure 2:
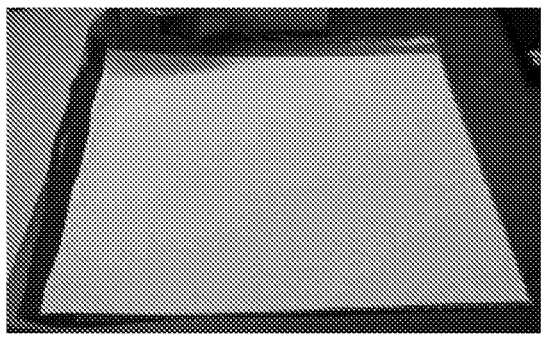
FIG. 2: A specific implementation of the architecture of FIG. 1, according to an embodiment of the invention.
Figure 2:
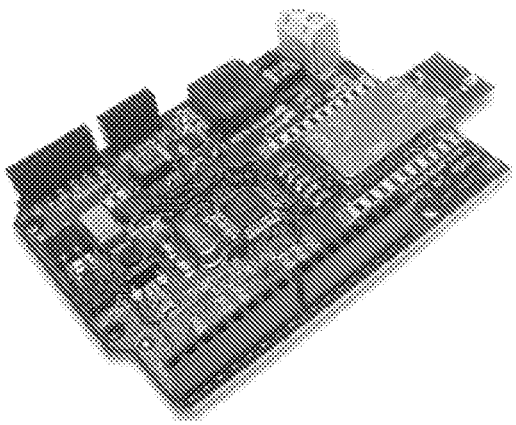
Figure 2:
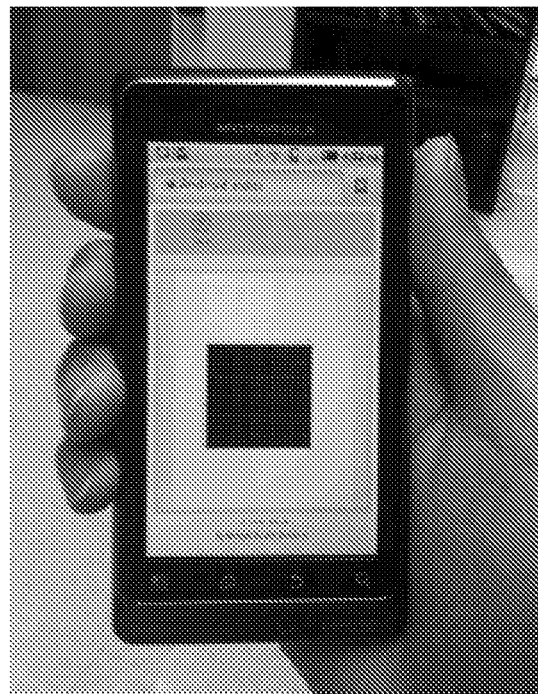

FIG. 2 shows a specific implementation of the architecture of FIG. 1, according to an embodiment of the invention. As shown in FIG. 2(*a*), a textile sensor array has a total sensor surface area of about 10 inch by about 10 inch, where a footprint of each pressure sensor is about ⅝ inch by about ⅝ inch, and a spacing between nearest-neighbor sensors is about ⅛ inch. Dimensions and spacing of the textile sensor array can be varied for other implementations. Referring to FIG. 2(*b*), a data sampling unit is implemented based on an Arduino Development board. A Bluetooth module is incorporated in the board to allow wireless transmission, and a driver circuit is based on an Arduino microcontroller for sensor array scanning, with a reconfigurable sampling frequency. Considering sitting position change frequency is typically lower than certain other bodily movements, the sampling frequency can be set at about 10 Hz, although other frequencies are contemplated. Data storage and analysis are performed on a data center shown in FIG. 2(*c*), including sitting position analysis, human movement index, and statistics of motion. Considering accessibility for mobile users, as shown in FIG. 2(*c*), the data center is implemented as a user-friendly software application that is developed for a mobile phone or another portable electronics device, which conveniently presents real-time feedback of pressure distributions and visualization of sitting positions.

Fabric-Based Pressure Sensor Array

A fabric-based pressure sensor array can be implemented using a textile sensor sheet that exhibits a piezoresistive effect, namely an electrical resistance of the sensor sheet varies in response to an applied force or pressure. In some embodiments, a textile sensor sheet can be implemented using textile fibers (e.g., synthetic or natural fibers) that are individually coated with an electrically conductive material, such as an electrically conductive polymer or a polymer with electrically conductive additives dispersed therein, and then knitted, woven, interlaced, bonded, or otherwise combined to form the sensor sheet. Examples of suitable electrically conductive polymers include nitrogen-containing aromatic polymers (e.g., polypyrroles, polycarbazoles, polyindoles, polyanilines, and polyazepines), sulfur-containing aromatic polymers (e.g., poly(3,4-ethylenedioxythiophene)), polythiophenes, polyfluorenes, polyphenylenes, polypyrenes, polyazulenes, polynapthalenes, polyacetylenes, and poly(p-phenylene vinylene). In other embodiments, a textile sensor sheet can be implemented using a pre-formed textile sheet, such as a woven or non-woven textile sheet, which is then coated, impregnated, or otherwise combined with an electrically conductive material to form the sensor sheet. During use, an initial resistance between a top surface and a bottom surface of a textile sensor sheet can be high, as a natural structure of the sensor sheet can be a relatively loose collection of fibers that are spaced by air gaps. When force or pressure is applied to either, or both, of the surfaces of the sensor sheet, interior fibers can be pressed together, thereby lowering the resistance. Note that the resistance between any two points on the same-side surface can be treated as effectively infinite, according to some embodiments. These electrical characteristics can be leveraged in the design of high-density and low-cost pressure sensor arrays. Other implementations of a textile sensor sheet are contemplated, such as by leveraging a piezoelectric effect in place of, or in conjunction with, a piezoresistive effect.

Figure 3:
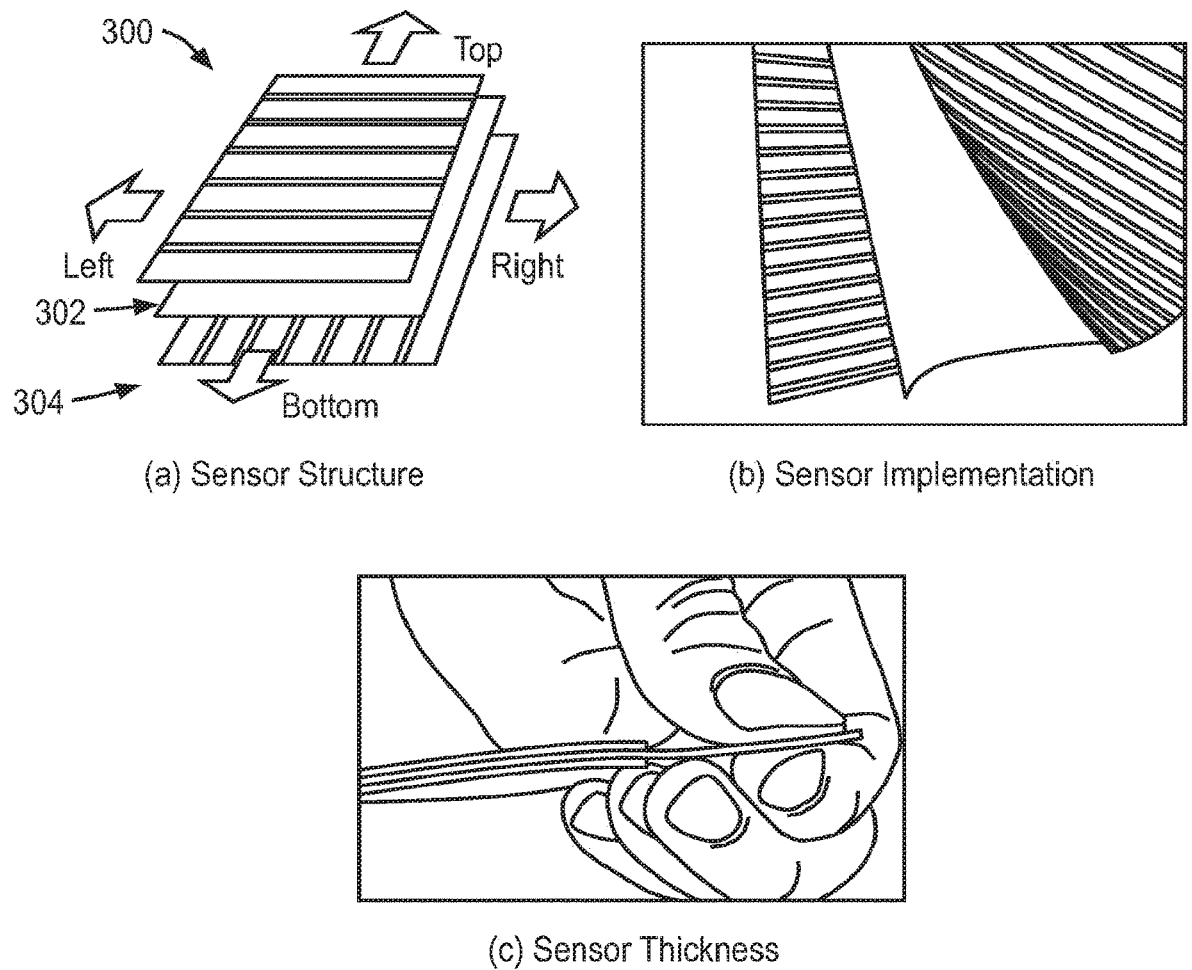
FIG. 3: A fabric-based pressure sensor array, according to an embodiment of the invention.

FIG. 3 shows a fabric-based pressure sensor array, according to an embodiment of the invention. The sensor array is implemented as a three layer, stacked structure, in which a middle layer 302 is a textile sensor sheet that is disposed between and laminated, bonded, or otherwise combined with a top layer 300 and a bottom layer 304. In the illustrated embodiment, the top layer 300 and the bottom layer 304 can be implemented using woven or non-woven textile sheets that are coated with an electrically conductive material to form elongated conductive strips. Specifically, these elongated strips correspond to conductive buses that are substantially parallel to one another in the top layer 300 and are substantially parallel to one another in the bottom layer 304. Suitable electrically conductive materials include electrically conductive polymers, polymers with electrically conductive additives dispersed therein, metals, and metal alloys, and suitable coating techniques include deposition, spraying, printing, and roll-to-roll coating. As shown in FIG. 3(*a*) and FIG. 3(*b*), the conductive buses of the top layer 300 are oriented relative to the conductive buses of the bottom layer 304 so as to cross over one another at crossing points or intersections. In the illustrated embodiment, the conductive buses of the top layer 300 are substantially orthogonal to the conductive buses of the bottom layer 304, although other crossing angles are contemplated, such as from about 1° to about 90°, from about 5° to about 90°, from about 20° to about 90°, from about 45° to about 90°, from about 90° to about 179°, from about 90° to about 175°, from about 90° to about 160°, or from about 90° to about 135°. Each intersection of a top conductive bus and a bottom conductive bus sandwiches a portion of the textile sensor sheet, thereby forming a pressure sensor at that location. In such manner, an array of pressure sensors is formed as a M×N matrix of pressure sensors, where M is a total number of the conductive buses of the top layer 300, and N is a total number of the conductive buses of the bottom layer 304. In the illustrated embodiment, M=N=16, and, therefore, a total number of pressure sensors in the array is 256. More generally, M can be the same as or different from N, and each of M and N can be 1 or more.

The sensor array of FIG. 3 provides a number of advantages. For example, multiple (i.e., M×N) pressure sensors can be formed through the use of a single textile sensor sheet of a continuous or unitary nature, thereby considerably reducing manufacturing burden that would otherwise result from the use of multiple, discrete textile sensor sheets that would have to be precisely aligned relative to top conductive buses and bottom conductive buses. The continuous or unitary nature of the sensor sheet can create challenges, such as in terms of crosstalk effects, but these challenges can be effectively addressed through the procedures described in the following sections. Specifically, crosstalk effects can be effectively mitigated in software, and such software decoupling affords advantages in terms of adjustability and maintaining manufacturing simplicity of the sensor array. Also, relative to alternative implementations in which each sensor has a separate Input/Output connector, a total number of Input/Output connectors required to individually address the M×N pressure sensors of FIG. 3 can be reduced to M+N, thereby reducing manufacturing burden and facilitating large-scale sensing applications. In the illustrated embodiment, M=N, and 2N Input/Output connectors can be used to address the N×N sensor array. Advantageously, the Input/Output connectors can be implemented using dual in-line package connectors or other pluggable connectors, which readily allow attachment and de-attachment of the sensor array. Moreover, as shown in FIG. 3(c), the sensor array can be relatively thin, with a total thickness in the range of about 0.1 mm to about 3 mm, such as from about 0.5 mm to about 2 mm or about 1.5 mm, which allows the sensor array to be flexible and lightweight for unobtrusive use.

Figure 4:
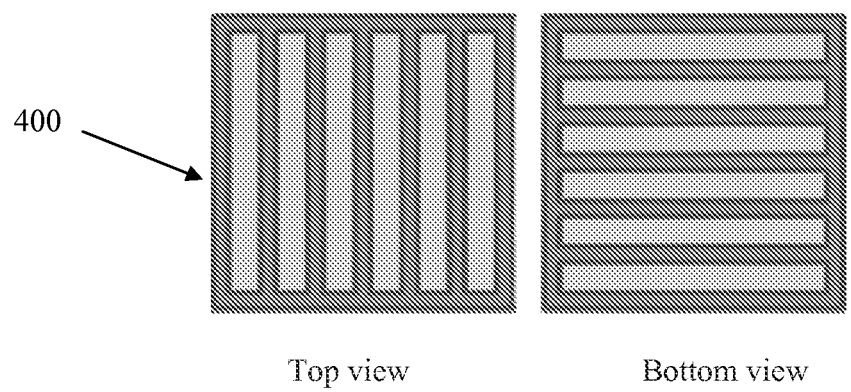
FIG. 4: A fabric-based pressure sensor array, according to another embodiment of the invention.

FIG. 4 shows a fabric-based pressure sensor array, according to another embodiment of the invention. The sensor array is implemented as a single layer structure, in which a textile sensor sheet 400 is coated with an electrically conductive material to form elongated conductive strips on a top surface and a bottom surface of the sensor sheet 400. Specifically, these elongated strips correspond to conductive buses that are substantially parallel to one another on the top surface and are substantially parallel to one another on the bottom surface. As shown in FIG. 4, the conductive buses of the top surface are substantially orthogonal to the conductive buses of the bottom surface, although other crossing angles are contemplated, such as from about 1° to about 90°, from about 5° to about 90°, from about 20° to about 90°, from about 45° to about 90°, from about 90° to about 179°, from about 90° to about 175°, from about 90° to about 160°, or from about 90° to about 135°. Each intersection of a top conductive bus and a bottom conductive bus sandwiches a portion of the textile sensor sheet 400, thereby forming a pressure sensor at that location. In such manner, an array of pressure sensors is formed as a M×N matrix of pressure sensors, where M is a total number of the conductive buses on the top surface, and N is a total number of the conductive buses on the bottom surface. In the illustrated embodiment, M=N=6, and, therefore, a total number of pressure sensors in the array is 36. More generally, M can be the same as or different from N, and each of M and N can be 1 or more. In addition to the advantages previously explained with reference to FIG. 3, the single layer implementation shown in FIG. 4 further streamlines a manufacturing process by omitting a top layer and a bottom layer, and can be even more flexible and lightweight for unobtrusive use, such as having a thickness from about 0.1 mm to about 1 mm, from about 0.2 mm to about 0.7 mm, or about 0.5 mm.

Figure 5:
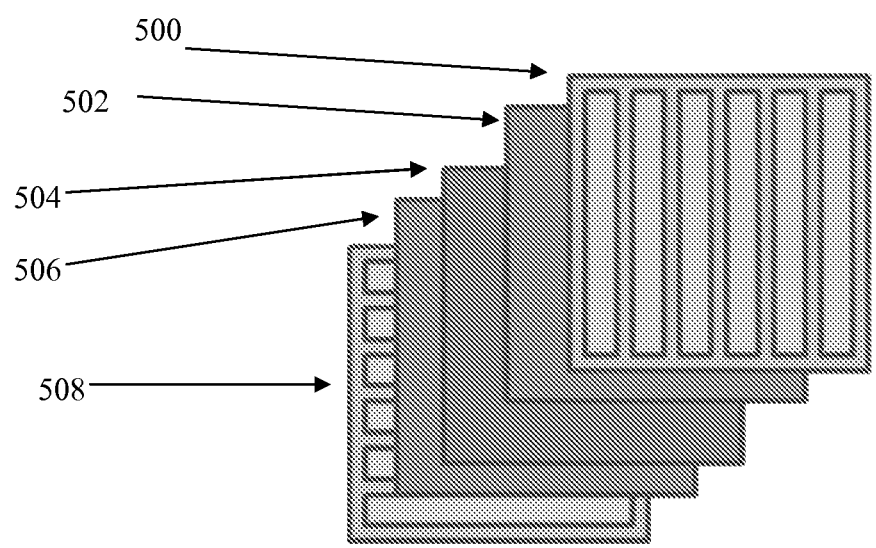
FIG. 5: A fabric-based pressure sensor array, according to another embodiment of the invention.

FIG. 5 shows a fabric-based pressure sensor array, according to another embodiment of the invention. The sensor array is implemented as a five layer stacked structure, in which a middle layer 504 is a textile sensor sheet that is disposed between and laminated, bonded, or otherwise combined with a top layer 500 and a bottom layer 508. The top layer 500, the sensor sheet 504, and the bottom layer 508 can be implemented as previously explained for FIG. 3. In the illustrated embodiment, the sensor array also includes a top isolation layer 502, which is disposed between the top layer 500 and the sensor sheet 504, and a bottom isolation layer 506, which is disposed between the sensor sheet 504 and the bottom layer 508. The isolation layers 502 and 506 serve to mitigate against crosstalk effects among neighboring sensors as a result of the continuous or unitary nature of the sensor sheet 504. In the illustrated embodiment, the isolation layers 502 and 506 can be implemented using a stress absorbing material, such as an elastomeric material. It is also contemplated that one of the isolation layers 502 and 506 can be omitted for other implementations.

Figure 6:
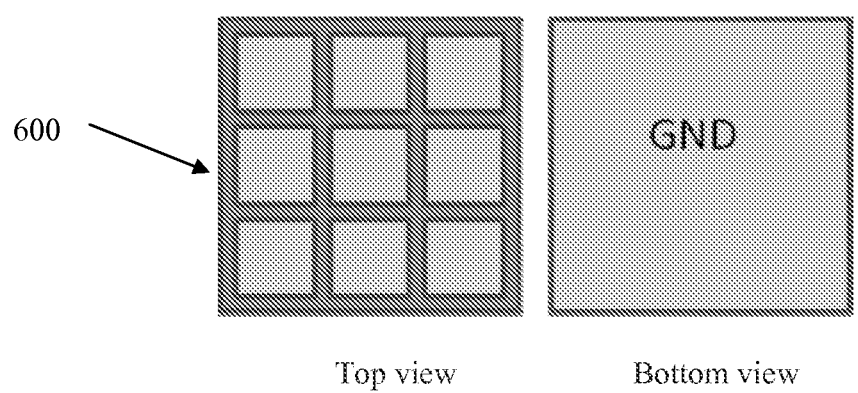
FIG. 6: A fabric-based pressure sensor array, according to another embodiment of the invention.

FIG. 6 shows a fabric-based pressure sensor array, according to another embodiment of the invention. The sensor array is implemented as a single layer structure, in which a textile sensor sheet 600 is coated with an electrically conductive material to form an array of contact pads on a top surface of the sensor sheet 600 and a ground contact pad on a bottom surface of the sensor sheet 600. It is also contemplated that the array of contact pads can be formed on the bottom surface, and the ground contact pad can be formed on the top surface. As shown in FIG. 6, the top contact pads occupy discrete regions and are isolated from one another, and each of the top contact pads and the ground contact pad is square-shaped, although other shapes are contemplated, such as circular, triangular, rectangular, pentagonal, other polygonal shapes, and other irregular shapes. The ground contact pad serves as a common ground connection and has a larger area so as to at least partially overlap each of the top contact pads. The area or size of the ground contact pad can be adjusted to provide or retain a desired flexibility to the sensor array. Each overlapping region of a top contact pad and the ground contact pad sandwiches a portion of the textile sensor sheet 600, thereby forming a pressure sensor at that location. In such manner, an array of pressure sensors is formed as a M×N matrix of pressure sensors, where M is a total number of rows of the top contact pads, N is a total number of columns of the top contact pads, and M×N=P is a total number of pressure sensors in the array. In the illustrated embodiment, M=N=3, and, therefore, the total number of pressure sensors in the array is 9. More generally, M can be the same as or different from N, and each of M and N can be 1 or more. Each pressure sensor can be connected to a data sampling unit via a separate (i.e., one-by-one) Input/Output connector. Therefore, each pressure sensor can be individually addressed substantially independent from neighboring sensors, with the substantial absence of crosstalk.

Other implementations of a fabric-based pressure sensor array are contemplated. For example, the configuration of the top contact pads and the ground contact pad of FIG. 6 can be extended to a three layer implementation as shown in FIG. 3 or a five layer implementation as shown in FIG. 5. As another example, a fabric-based pressure sensor array can include a sensor sheet that is implemented as a mesh, net, or web-like structure, thereby affording high flexibility and being conformable to fit a particular part of a human body, such as a foot. To fabricate such a sensor array, conductive wires can be coated on a mesh layer, and a thickness of the conductive wires can be adjusted to change a flexibility or rigidity of the sensor array. The conductive coating can be fabricated on the mesh layer, or subsequently attached to the mesh layer, and a material of the coating can be an electrically conductive polymer or copper fiber-based wires.

Data Sampling Unit

Figure 7:
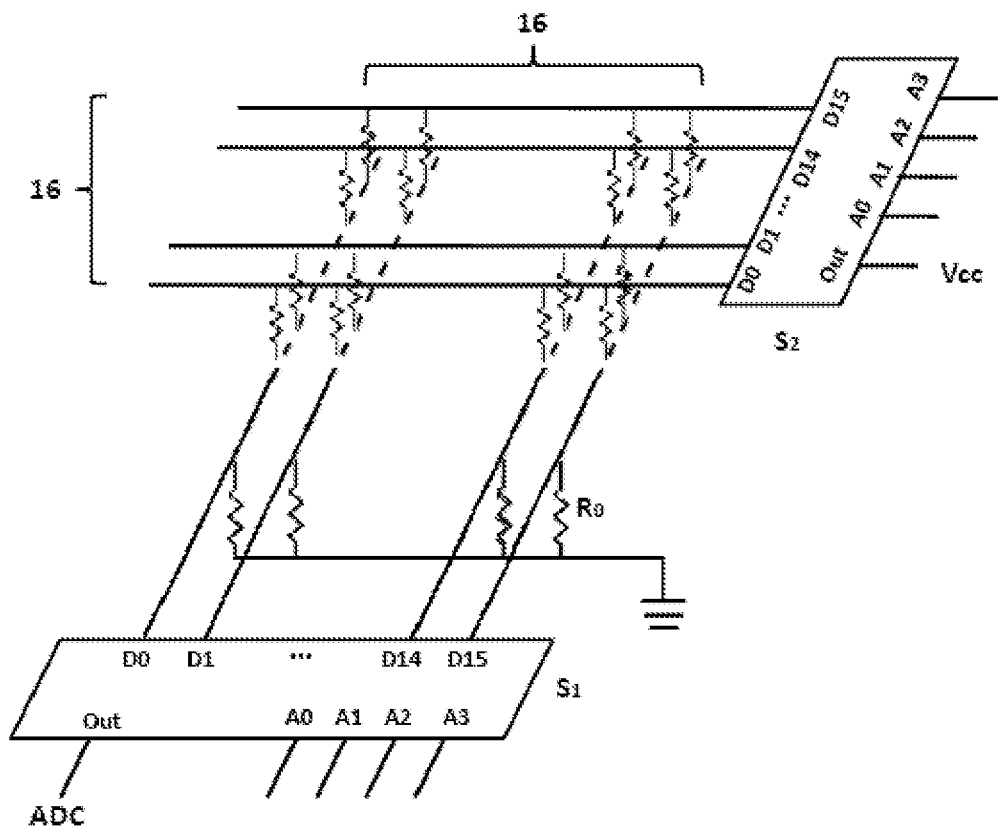
FIG. 7: A peripheral circuit for sensor array scanning, according to an embodiment of the invention.

FIG. 7 shows a peripheral circuit for scanning a textile sensor array, which can be included in a data sampling unit in accordance with an embodiment of the invention. Each conductive bus on a bottom layer of the sensor array is connected to an analog-to-digital converter ("ADC") via an analog switch module S1 and to ground via an offset resistor Ro. Each conductive bus on a top layer of the sensor array is connected to a voltage supply $V_{cc}$ via an analog switch module S2. The analog switch modules S1 and S2 operate in conjunction to selectively address a specific pressure sensor, and a scanning sequence is synchronized by a microcontroller (not shown), which also can be included in the data sampling unit. For example, when S2 connects a selected bus i on the top layer to $V_{cc}$ and S1 connects a selected bus j to the ADC, the ADC can read a voltage through a pressure sensor located at an intersection of bus i and bus j, namely located at row i and column j, which voltage can be denoted as $V_{ij}$. In such manner, the peripheral circuit has random accessibility for reading an arbitrary sensor within the sensor array. Also, the single ADC can be shared among multiple sensors, thereby reducing manufacturing burden and facilitating large-scale sensing applications relative to alternative implementations in which each sensor has a separate ADC to sample a sensor output. In between readings or when S1 and S2 channels are deactivated, a ground voltage or another well-defined voltage can be applied to row-wise and column-wise connections. Also, although not shown in FIG. 7, solid-state relays (e.g., optically coupled relays) or other types of switching devices can be included in the row-wise and column-wise connections to mitigate against leak currents that can otherwise result in inaccuracies or interference when reading an individually addressed sensor.

Data Center

Figure 8:
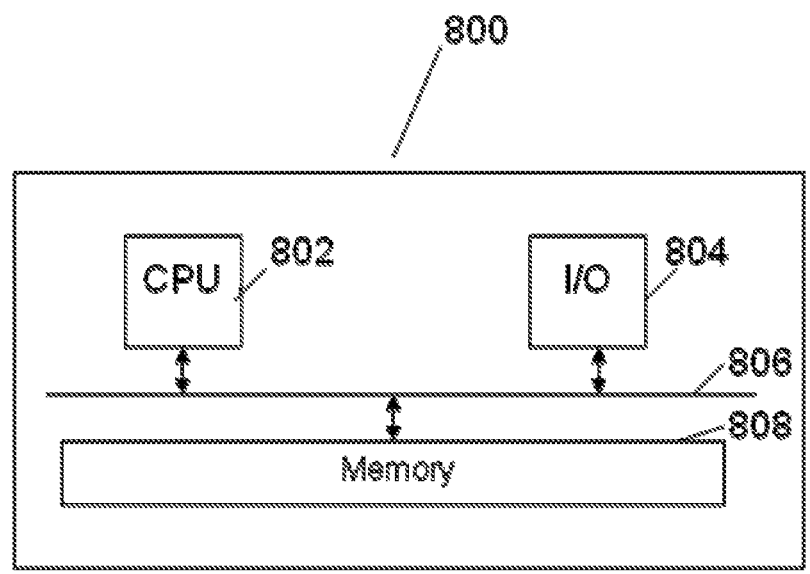
FIG. 8: A data center, according to an embodiment of the invention.

FIG. 8 shows a data center 800 implemented in accordance with an embodiment of the invention. Depending on a specific application, the data center 800 can be implemented as, for example, a portable electronics device, a client computer, or a server computer. Referring to FIG. 8, the data center 800 includes a central processing unit ("CPU") 802 that is connected to a bus 806. Input/Output ("I/O") devices 804 are also connected to the bus 806, and can include a keyboard, mouse, display, and the like. An executable program, which includes a set of software modules for performing calibration and posture recognition procedures described in the following sections, is stored in a memory 808, which is also connected to the bus 806. The memory 808 can also store a visualization module to generate alerts or other visual presentations of recognized postures.

Challenges in Fabric-Based Sensor Array Data

When a user applies forces on a sensor array, its output can be affected by factors in addition to a posture of the user. Specifically, the sensor array output can be interfered by various factors, which can create challenges in analyzing the output. Particularly when the sensor array is incorporated into apparel or other textile products, other uncertainties from the environment can render the output even more fuzzy. In some embodiments, four dominant factors of signal distortion or interference arise from offset, scaling, crosstalk, and rotation, where offset and scaling are typically caused by array-to-array variability or uncertainty, and crosstalk and rotation typically belong to within-array variability or uncertainty.

(1) Offset: In an ideal case, an initial pressure on each sensor should be zero. However, due to a sandwiched structure of a fabric-based sensor array in some embodiments, an initial offset pressure can be present, and its value can depend on a particular assembling method of the sensor array. If three layers are laminated tightly, for example, an offset pressure value can be high. If the three layers are laminated loosely, for example, the offset pressure value can be low. As can be appreciated, different sensor arrays can have different assembling status, and this type of manufacturing variability yields different offset pressure values from array-to-array.

(2) Scaling: Characteristics of a fabric-based sensor array can yield relatively large resistivity variations. Even if the same forces are applied to two sensors, their outputs are not necessarily the same. As a result, it can be difficult to define a general look-up table that establishes the relationship between an applied force and a sensor output in all cases.

Figure 9:
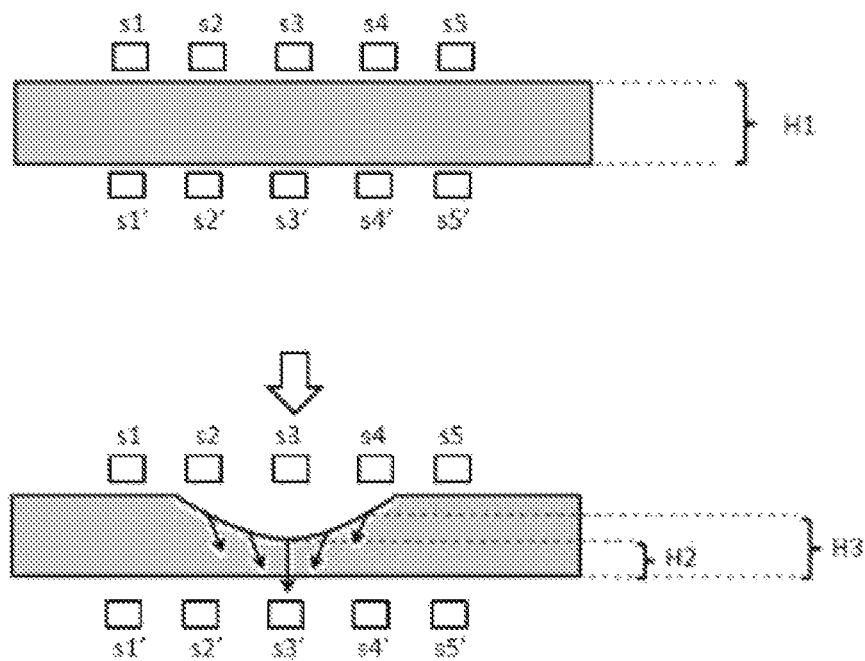
FIG. 9: Crosstalk effect in a fabric-based pressure sensor array, according to an embodiment of the invention.

(3) Crosstalk: The crosstalk effect can be one of the most challenging issues to address in a fabric-based sensor array, and can be particularly pronounced given the continuous or unitary nature of a textile sensor sheet in some embodiments. Due to close distances between sensors, neighboring sensors can be mechanically coupled together in such a sensor sheet. As shown in FIG. 9, a sensor sheet is initially uniform, and a thickness value of each sensor is initially H1. Once a force is applied on sensor S3, its thickness is reduced to H2. In conjunction, neighboring sensors also are compressed, with sensor values of S2 and S4 changing along with S3. As shown in FIG. 9, the thickness of S2 and S4 is reduced to H3, although no direct force is applied on these neighboring sensors. This effect indicates that a sensor output is not solely linked with an applied force, thereby creating challenges in analyzing the output.

Figure 10:
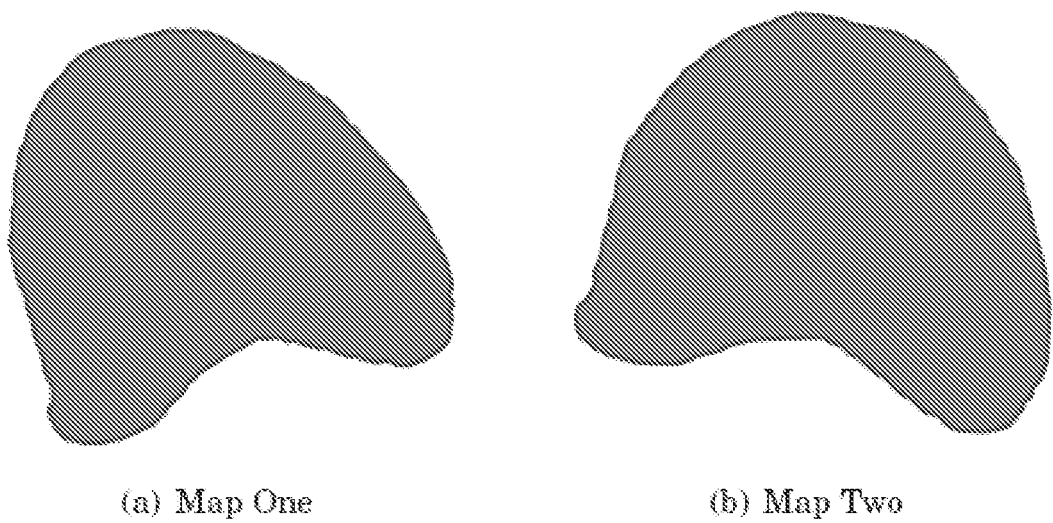
FIG. 10: Pressure map rotation, according to an embodiment of the invention.

(4) Rotation: Even if a user lies or sits on a fabric-based sensor array with the same posture, a resulting pressure map can vary according to different orientations of the user. FIG. 10 shows two pressure distributions with the same sitting posture but different sitting orientations. Although the pressure map in FIG. 10(a) is similar to that in FIG. 10(b), it can be difficult to match these pressure maps using typical pattern recognition approaches, since rotation is generally harder to handle compared to translation and scaling.

In this section, challenges for fabric-based sensor arrays are presented. To achieve high performance in applications, the above-noted factors should be addressed effectively. In the next section, a calibration procedure is presented to improve the quality of sensor array data.

Sensor Calibration (1) Preliminary Modeling:

To make inferences for applications, such as sitting position analysis, it is desirable to obtain accurate measurements from a sensor array. Towards addressing the variability or uncertainty factors presented in the previous section, a sensor can be modeled to extract a relationship between an applied force $F_a$ and a sensor output $V_o$.

Figure 11:
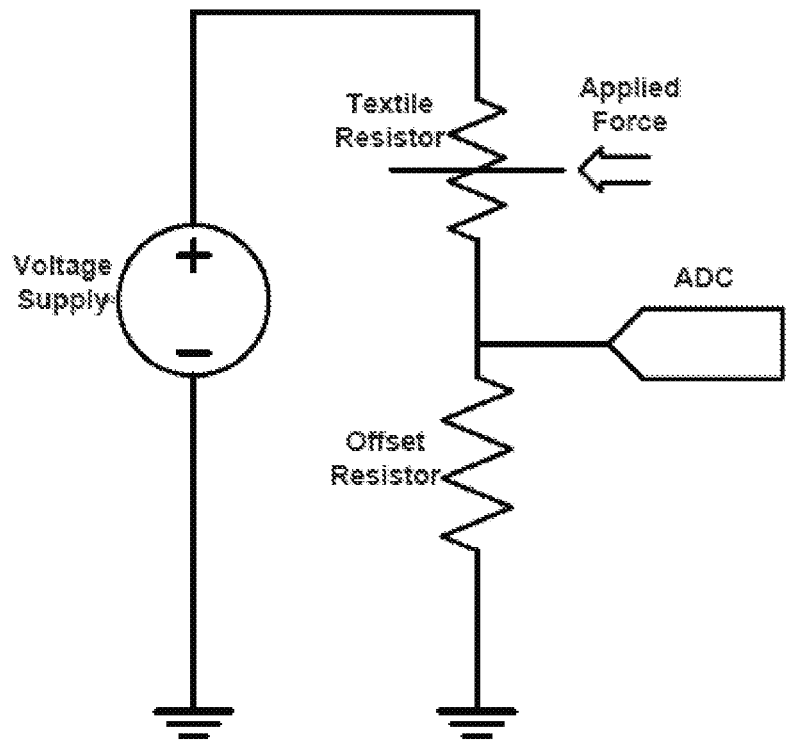
FIG. 11: Parametric modeling of a single fabric-based pressure sensor, according to an embodiment of the invention.

FIG. 11 models certain intrinsic parameters in a single textile sensor. A textile resistor, $R_t$, and an offset resistor, Ro, are connected serially in the illustrated embodiment. One end is connected to a voltage supply, $V_s$, and another end is connected to ground, GND. A middle joint point is connected to an analog-to-digital converter, ADC, for reading a sensor output $V_o$. According to mechanical characteristics of the textile sensor, the applied force, $F_a$, is approximated to be inversely proportional to the sensor resistor, $R_t$:

$$R_t = \frac{C}{F_a} \tag{1}$$

where C is a constant. Therefore, based on the parametric model of FIG. 11, a relational expression can be derived between the sensor output, $F_o$, and the applied force, $F_a$:

$$F_a = \frac{C \times V_o}{R_t \times (V_s - V_o)} \tag{2}$$

From Equation (2), it can be observed that the applied force is related in a non-linear fashion to the ADC reading, and this non-linearity can create challenges in analyzing the ADC reading.

(2) Markov Random Field ("MRF")/Gibbs Distribution Re-Sampling Procedure:

One contemplated approach to calibrate textile sensors across an array is to establish a pressure-resistance look-up table to model the sensors via repeated voltage measurements under a number of applied pressures. However, there can be difficulties involved with this approach for some embodiments. For example, even though measurements of an output voltage can be performed one-by-one for each sensor, it can be difficult to account for the crosstalk effect in the output voltage if neighboring sensors also are subjected to pressure at the same time. Furthermore, a pressure-resistance relationship can change across different fabric-based sensor arrays, as a result of manufacturing variations. Therefore, establishing a pressure-resistance relationship can involve an ad-hoc modeling, which can have restricted applicability to a particular sensor array being calibrated.

In some embodiments, a re-sampling statistics procedure based on the MRF/Gibbs distribution is used to calibrate variability or uncertainties in a sensor array, instead of establishing an ad-hoc modeling for each textile sensor. The procedure involves determining an up-threshold, $Th_{up}$, and a down-threshold, $Th_{dn}$, for the sensor array to determine which sensors across the array should be calibrated. Firstly, the following procedure is used to determine which sensor outputs are outliers that should be re-sampled:

TABLE I

Re-sampling Procedure

1: /* Step 1: Data Annotation and Setup */
2: Initial arrayed sensor reading: ArrayValue(i, j) denotes the sensor value located at (i, j)
3: Calculate the up-threshold value $Th_{up}$ and the down-threshold. value $Th_{dn}$
4: Decide the re-sampling table Mask; where Mask(i, j) = 1 means that the pressure value is needed to be re-sampled, Mask(i, j) = 0 means that the pressure value is NOT needed to be re-sampled
5:
6: /* Step 2: $Th_{up}$ and $Th_{dn}$ setup */
7: $Th_{up}$ = mean(ArrayValue) + std(ArrayValue);
8: $Th_{dn}$ = mean(ArrayValue) − std(ArrayValue);
9:
10: /* Step 3: Re-sampling Table Calculation*/
11: for i = 1 to n do
12:   for j = 1 to n do
13:     if ArrayValue(i, j) > $Th_{up}$ and ArrayValue(i, j) < $Th_{dn}$ then
14:       Mask(i, j) = 1;
15:     else
16:       Mask(i, j) = 0;
17:     end if
18:   end for
19: end for
20:

Here, it is assumed that noise in a sensor array without any imposed pressure is according to a Gaussian distribution. Once having the re-sampling table Mask, pressure values within the threshold range are filtered by randomly initializing the values. Next, re-sampling is performed according to the MRF/Gibbs probability distribution as follows:

$$P(X = x) = \frac{1}{Z(\beta)} e^{-\beta E(x)} \qquad (3)$$

Figure 12:
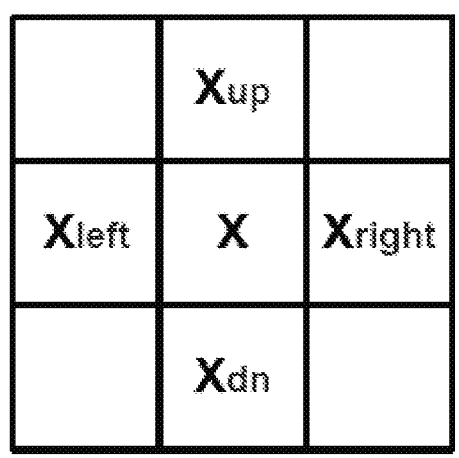
FIG. 12: An illustration of a sensor x and its neighboring sensors, according to an embodiment of the invention.

In Equation (3), Z is used for normalizing the probability distribution, E is an energy function derived from neighboring pressure values around x, and β is a free variable for finer tuning, such as using a simulated annealing method. In some embodiments, β is tuned by decreasing its value monotonously by a constant factor. A norm-2 energy function can be used as a summation of squared differences between x and its neighbors, and a neighborhood context is shown in FIG. 12. Therefore, the energy function used to calculate the probability density function of x can be represented as:

$$pdf(x) = e^{-\beta((x_{up}-x)^2 + (x_{dn}-x)^2 + (x_{left}-x)^2 + (x_{right}-x)^2)} \qquad (4)$$

In this procedure, whenever an outlier pressure value is detected outside of $Th_{dn}$ and $Th_{up}$, the probability distribution of the pressure value is re-computed or otherwise updated, and a new pressure value is generated by the re-sampling formulation of Equation (3). Scanning all outlier pressure values once is called 1-sweep. After a few sweeps, an outlier pressure value will become closer to its neighboring pressure values because the probability distribution will become narrower when the energy decreases. In other words, updated sampling values drawn from the updated probability distributions will become similar to neighboring pressure values. In conjunction, the threshold values, $Th_{dn}$ and $Th_{up}$, can be iteratively adjusted based on the updated probability distributions. According to this procedure, a heavier pressure point on the sensor array can have more impact on its neighbors, meaning that pressure values inside an object area can be boosted to a higher value close to an average pressure value of the imposed object. This conclusion can be confirmed by the follow proof.

Given that a boundary pressure value can be determined as follows:

$$pdf(x) = e^{-\Sigma_i(x_{neighbor_i} - x)^2} \qquad (5)$$

Its maximum likelihood can be obtained by its differentiation equation:

$$\frac{\partial pdf}{x} = 0 \qquad (6)$$

$$\sum (x_{neighbor_i} - x)^2 = 0 \qquad (7)$$

Equation (7) indicates that x is more likely to be a value around an average of its neighbors. After applying the calibration procedure, holes or gaps of a pressure map that might otherwise be present inside an uniformly weighted object area can be filled. Also, hotspots or high pressure regions of a pressure map, such as caused by fabric wrinkles or uneven underlying environment of a sensor array, can be mitigated or removed through averaging across neighbors According to the calibration procedure, a smaller number of noisy pressure values can affect the summation result. Hence, a resulting pressure measurement can be closely linear along with a weight of an object on the sensor array. Since the threshold range selection is adaptive for the particular sensor array and outlier pressure values can be selectively re-sampled and adjusted, the calibration procedure can avoid over-smoothing a pressure map, and does not require manually tuning of threshold values.

In this section, a re-sampling calibration procedure is presented to iteratively adjust a threshold range based on updating a probability distribution. After the calibration procedure, sensor measurements have a higher precision, and a shape of an object imposed on a sensor array is also preserved.

Posture Recognition

Contemplated approaches for posture recognition include template-based procedures to distinguish between different postures, a Naive Bayes Network to train data and select featured sensors for classification, eigenvectors, Bayesian networks, logistic regression, nearest neighbor procedures for classification, as well as other types of machine learning procedures.

Another approach involves the use of an improved procedure to efficiently perform posture recognition, while addressing variability or uncertainties characteristic of a fabric-based sensor array.

(1) Data Preprocessing for Crosstalk:

Crosstalk is a cluster-based effect that can affect data as a whole. Assuming there are n textile sensors, the crosstalk effect among the n sensors can be expressed as:

$$F_{1 \times n} C_{n \times n} \doteq D_{1 \times n} \qquad (8)$$

where $D_{1 \times n}$ denotes n sensor values, $F_{1 \times n}$ denotes the force applied on the n sensors, and $C_{n \times n}$ denotes a F-to-D transformation matrix including the crosstalk effect. When $f_i$ is applied on a sensor i, the impact on a sensor j can be calculated by:

$$f_i c_{ij} = d_j \qquad (9)$$

To assess the crosstalk effect, an unit force can be applied on a single sensor i, denoted as $F_{ei}$, and an output can be measured from each sensor, $D_{ei}$, which can be expressed as an 1×n vector. Based on Equation (8), the following relationship is obtained:

$$C_{n \times n} = \begin{bmatrix} D_{e1} \\ D_{e2} \\ \cdot \\ \cdot \\ \cdot \\ D_{en} \end{bmatrix} \qquad (10)$$

Based on measurements, it is observed that the transformation matrix $C_{n \times n}$ is typically sparse, and most or all elements on the diagonal are typically non-zero. Therefore, an inverse matrix of $C_{n \times n}$ can be calculated, denoted as a decoupling matrix $C^{-1}$, and a pressure map without crosstalk (or with reduced crosstalk) can be determined by applying the decoupling matrix according to the following transformation:

$$F_{1 \times n} \doteq D_{1 \times n} C_{n \times n}^{-1} \qquad (11)$$

(2) Data Representation:

To facilitate posture recognition, a suitable procedure for data representation can be implemented for some embodiments. Instead of processing a pressure map (e.g., two-dimensional pressure image) directly, the pressure map can be converted into a pressure profile or sequence (e.g., one-dimensional time series). In general, a number of advantages can result from processing one-dimensional sequential data. First, the dimensionality of the data is reduced, thereby reducing complexity and enhancing speed of a posture recognition procedure as compared to processing of two-dimensional pressure images. Second, it can be easier to tackle rotation when processing one-dimensional sequential data. And with sequential data, certain distortions, including offset and scaling, can be reduced or eliminated through z-normalization:

$$x'_n = \frac{x_n - \mu}{\sigma} \qquad (12)$$

where $\mu$ is an expectation value of the sequential data, and $\sigma$ is a variance of the sequential data. However, it is also contemplated that posture recognition can be performed by directly processing pressure maps, such as using image matching or classification procedures.

Figure 13:
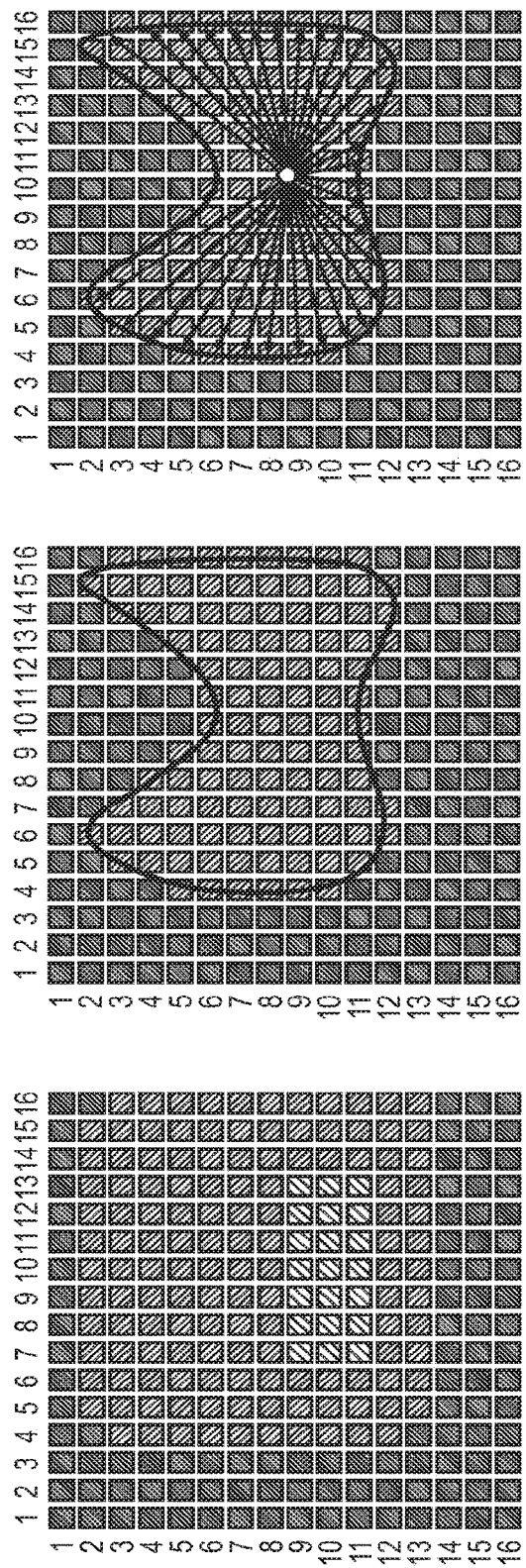
FIG. 13: Data representation procedure, according to an embodiment of the invention.
Figure 13:
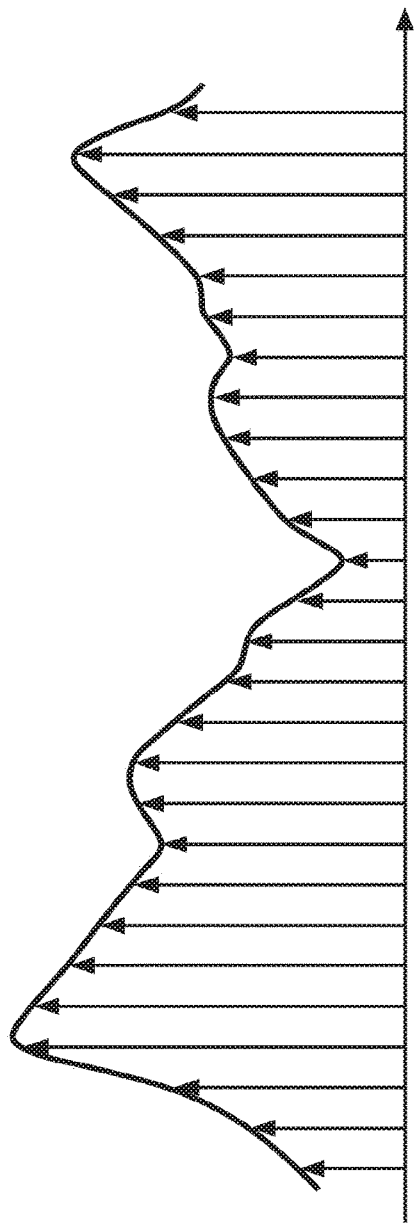

In some embodiments, a procedure for data representation includes the following operations:

Operation 1: Obtain calibrated data as a two-dimensional pressure map, as shown in FIG. 13(a).

Operation 2: As shown in FIG. 13(b), a canny edge detector is applied to the pressure map to obtain a binary image.

Operation 3: As shown in FIG. 13(b), an outline curve or boundary of the binary image is determined. In some embodiments, the outline curve is generally a closed form due to the shape of a human body.

Operation 4: Distances are determined between various points on the outline curve and an image center (or another reference point in the binary image), as shown in FIG. 13(c). The points on the outline curve can be regularly or irregularly spaced along the curve, and can be specified as intersections of a line segment rotated through regular or irregular angular increments relative to the image center.

Operation 5: The determined distances are represented as values on the y-axis of an one-dimensional time series, as shown in FIG. 13(d).

In such manner, two-dimensional pressure distribution information is converted to one-dimensional pressure sequences. In the next subsection, a posture recognition procedure is presented to exploit this one-dimensional pressure representation.

(3) Pressure Sequence Matching using Dynamic Time Warping ("DTW"):

In some embodiments, DTW is used to recognize different postures of a user. Target pressure sequences can be derived from corresponding pressure maps while the user is lying or sitting on a fabric-based sensor array, and, using DTW, the target pressure sequences can be compared with reference pressure sequences (which are associated with difference pre-determined postures) to determine whether there is a match. As can be appreciated, DTW involves a similarity evaluation for two time series. Compared to Euclidean distance, DTW is generally more robust, allowing similar patterns to be matched even if they are out of phase. Because rotation in a two-dimensional pressure map can be viewed as a phase shift in one-dimension, DTW can recognize a posture under different orientations of the user. However, it is also contemplated that pattern matching can be performed using other procedures, such as Euclidean distance or Levenshtein distance.

According to DTW, two pressure sequences can be denoted as:

$$S = [s_1, s_2, s_3, \ldots, s_i, \ldots, s_n]$$

$$T = [t_1, t_2, t_3, \ldots, t_j, \ldots, t_m] \qquad (13)$$

Figure 14:
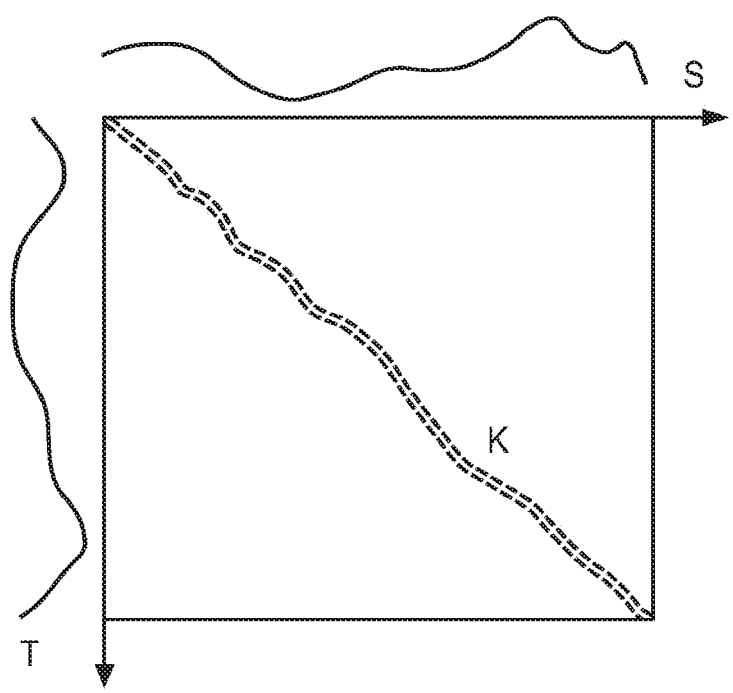
FIG. 14: A warping example of two pressure profile sequences, according to an embodiment of the invention.

To evaluate the similarity of these two sequences, DTW derives a n by m matrix D, where $d_{ij} = (s_i - t_j)^2$. Each element $d_{ij}$ denotes the similarity between $s_i$ and $t_j$. A continuous and monotonic path W from $d_{11}$ to $d_{mn}$, is then determined so as to minimize cost. The time and space complexity of DTW (S,T) is $\Theta(mn)$. FIG. 14 shows an example of a DTW-based similarity evaluation between two pressure sequences.

In some embodiments, a speed of a DTW-based similarity evaluation can be enhanced by setting bounds to reduce a DTW search space. One approach involves tuning parameters according to a procedure similar to LB_Keogh. Further details of LB_Keogh can be found in Keogh et al., "Lb keogh supports exact indexing of shapes under rotation invariance with arbitrary representations and distance measures," *ACM International Conference on Very Large Data Bases*, pp. 56-78 (2006), the disclosure of which is incorporated herein by reference in its entirety. Another approach involves adaptive bounding values according to a sequence itself, without relying on parameters to be tuned. Given any 2r length subsequence $S'=[s_{i-r}, s_{i+r}]$ in S, an upper bound of S' is $U_i$, and a lower bound of S' is $L_i$. The calculation of $U_i$ and $L_i$ can be performed as follows:

$$U_i = 1.5 \times s_i$$

$$L_i = 0.75 \times s_i \quad (14)$$

With these adaptive bounding values, DTW(S,T) becomes:

$$DTW(S, T) = \sqrt{\sum \begin{cases} (t_i - U_i)^2 & \text{if } t_i > U_i \\ (t_i - L_i)^2 & \text{if } t_i < L_i \\ 0 & \text{otherwise} \end{cases}} \quad (15)$$

It is noted that a DTW similarity evaluation can regress to Euclidean distance when r is 1.

EXAMPLES

The following examples describe specific aspects of some embodiments of the invention to illustrate and provide a description for those of ordinary skill in the art. The examples should not be construed as limiting the invention, as the examples merely provide specific methodology useful in understanding and practicing some embodiments of the invention.

Example 1

Initial Testing of Pressure Sensor Array: In one experiment, a fabric-based pressure sensor array was implemented as a bed sheet, namely a Smart Bed Sheet, which was tested to demonstrate it can capture a pressure map when force is applied. A 16×16 sensor array was used to capture the pressure map.

Figure 15:
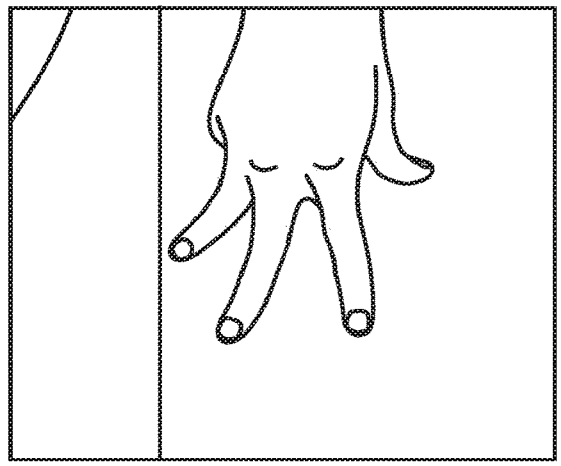
FIG. 15: Image of four fingers with pressure maps from a fabric-based pressure sensor array, according to an embodiment of the invention: (a) Four fingers on pressure sensors; (b) Captured pressure map with crosstalk effect; and (c) Pressure map without crosstalk effect after data preprocessing.
Figure 15:
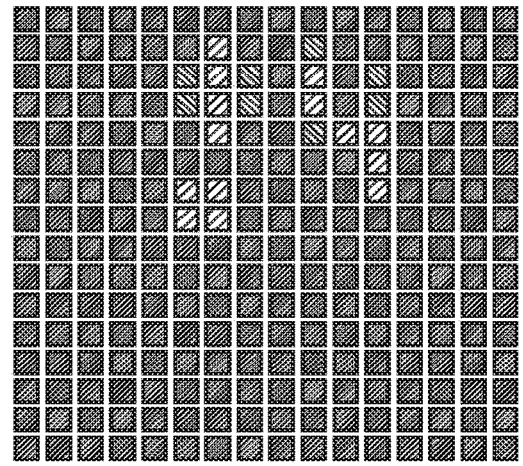
Figure 15:
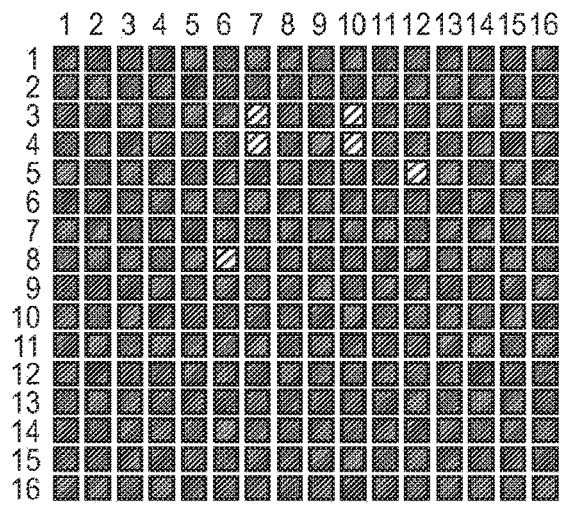

When four fingers are pressing on the sheet as shown in FIG. 15(a), outputs of pressure sensors under those fingers will change and can provide a pressure map as shown in FIG. 15(b). It can be observed that neighboring pressure sensors around the fingers can also capture the applied pressure due to the crosstalk effect. As such, an efficient data preprocessing procedure is performed to eliminate or reduce the undesired crosstalk effect, and a resulting pressure map is shown in FIG. 15(c).

Figure 16:
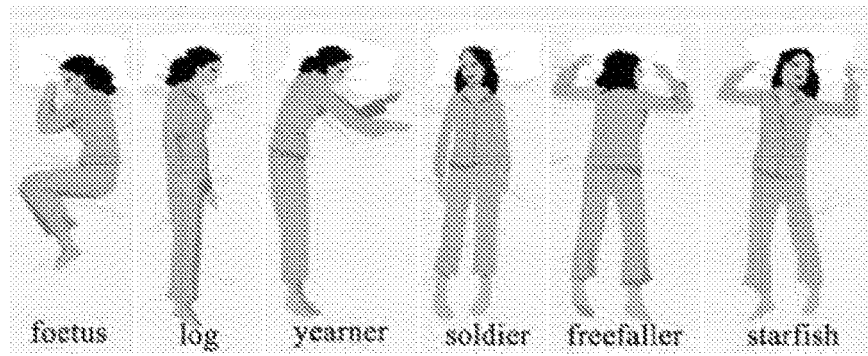
FIG. 16: Six common sleeping positions, according to an embodiment of the invention.

Testing of Smart Bed Sheet: To evaluate an accuracy of a Smart Bed Sheet system, a pilot was performed using twenty subjects, including ten males and ten females. Each participant was asked to lay on the Smart Bed Sheet with six common sleeping positions as shown in FIG. 16, including fetus (or foetus), log, yearner, soldier, freefaller, and starfish.

When a participant is lying on the Smart Bed Sheet, pressure sensors can capture a pressure map contour for real-time monitoring. In addition, the system can recognize a sleeping position of the participant by matching with contours of the six predesigned common positions using procedures set forth above. Therefore, if a patient stays in the same sleeping position for a prolonged period of time, the system can automatically alert a healthcare practitioner to change the sleeping position for ulcer prevention.

To evaluate the performance of the Smart Bed Sheet system for sleeping position recognition, two approaches were used to make a comparison as set forth in Table(II): self-training and general training. As for the self-training approach, each participant was asked to lay on the Smart Bed Sheet to establish a correlation between a specific pressure map and a corresponding sleeping position for that participant. In this approach, the Smart Bed Sheet can achieve up to about 96% accuracy rate. When the Smart Bed Sheet system was trained with overall data for all participants, the accuracy rate was reduced somewhat to about 89%. Moreover, under the general training approach, it was observed that the accuracy rate for males (about 93%) is higher than that for females (about 85%). Without wishing to be bound by a particular theory, this difference in accuracy rates may result from a greater weight of the male participants.

TABLE II

Comparison of Accuracy Rates for Smart Bed Sheet

|  | Self-training | General Training |
| --- | --- | --- |
| Accuracy Rate | 96% | 89% |
|  | Male | Female |
| Accuracy Rate | 93% | 85% |

Example 2

Experimental Setup: A fabric-based pressure sensor array was implemented as a seat cushion, namely an eCushion. To evaluate the accuracy of the eCushion system, a pilot was performed using ten subjects, including six males and four females.

Figure 17:
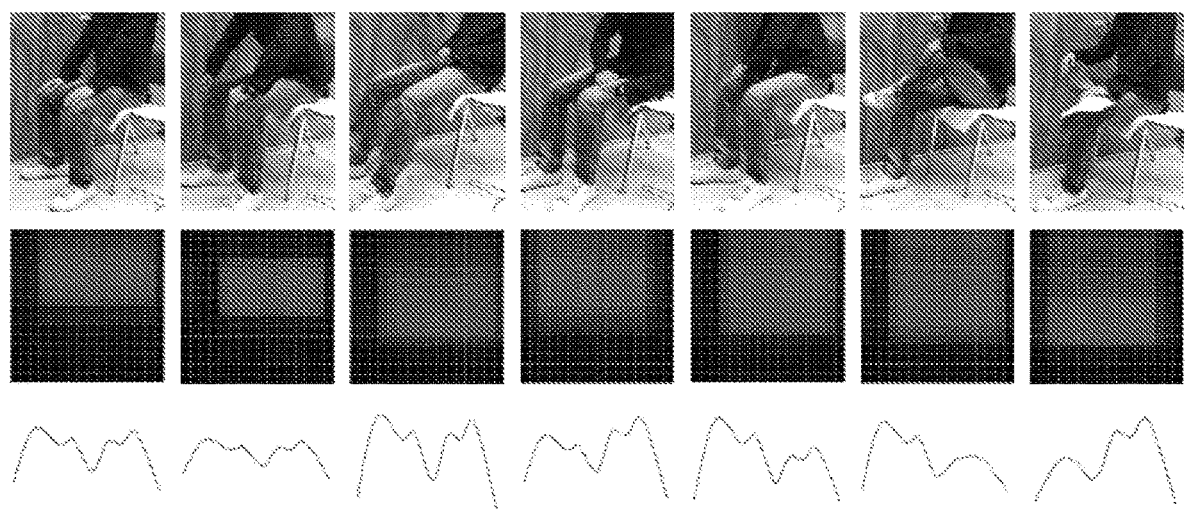
FIG. 17: Sitting Position Analysis, according to an embodiment of the invention: Seven sitting positions (top) are evaluated, and each pressure map (middle) is converted to a corresponding pressure profile sequence (bottom).

Each participant was asked to sit on the eCushion with seven predesigned sitting positions for five rounds. The captured data was used as training data. The seven positions included 1) situp, 2) forward, 3) backward, 4) left lean, 5) right lean, 6) right foot over left, and 7) left foot over right. FIG. 17 shows an example for one participant to explain the procedure of data acquisition and preprocessing. The images on the top row of FIG. 17 show the seven sitting positions. The middle row images show the corresponding pressure map of each position. Each pressure map includes a total of 256 data samples or pixels. At the bottom row of FIG. 17 are pressure profiles extracted from the pressure maps. Each sequence is evaluated and classified with DTW, implemented with LB_Keogh to set bounds and speed up processing. A pressure-resistance look-up table was used for calibration purposes.

Recognition Results: Two evaluation approaches are performed for sitting position analysis. The first approach involved position recognition based on self-training data. As set forth in Table III, the accuracy rate on self-training can be about 92%. The second approach involved position recognition based on general training data, which can be considered more fair and objective. As set forth in Table III, the accuracy rate on general training can be about 79% on average. These experimental results demonstrate that the eCushion system can achieve a high accuracy rate in recognizing sitting positions.

TABLE III

Experimental Results

| | Self-training | General Training |
|---|---|---|
| Accuracy Rate | 92% | 79% |

Example 3

Experimental Setup: A fabric-based pressure sensor array was implemented as a seat cushion, namely an eCushion. To evaluate the effectiveness of the eCushion system, a pilot was performed on twenty-five subjects, including fifteen males and ten females.

Each participant was asked to sit on the eCushion with seven common sitting positions. The captured data was used as training data. The seven positions included 1) situp, 2) forward, 3) backward, 4) left lean ("LL"), 5) right lean ("RL"), 6) right foot over left ("RFOL"), and 7) left foot over right ("LFOR"). Each pressure map includes a total of 256 data samples or pixels, and pressure profiles were extracted from the pressure maps. Each sequence is evaluated and classified with DTW, implemented with an adaptive bounding approach. A MRF/Gibbs distribution re-sampling approach was used for calibration purposes.

Recognition Results: The experimental results are set forth in Table IV. The results are listed for all sitting positions with precision (i.e., percentage of classified instances that are relevant) and recall (i.e., percentage of relevant instances that are classified) calculations. The overall accuracy over all sitting positions is about 87.4%, which outperforms the results set forth in Example 2. It is believed that the improvement in accuracy results (at least in part) from the re-sampling calibration, which can more effectively address uncertainties in the fabric-based sensor data. The results also reveal that "right lean" yielded the best precision, and "forward" yielded the best recall. Furthermore, it is observed that "sit-up," "forward," and "backward" can be viewed as related in a similar group. Data samples for these positions are rarely (or never) misclassified into other positions, but exhibit a tendency for misclassification with each other within the group. This tendency indicates that these three sitting positions share various common features. This insight can be helpful to further optimize recognition accuracy while considering these sitting positions specifically.

TABLE IV

Experimental Results: Precision versus Recall

| | situp | forward | backward | LL | RL | LFOR | RFOL | total | recall |
|---|---|---|---|---|---|---|---|---|---|
| situp | 85 | 7 | 8 | 0 | 0 | 0 | 0 | 100 | 85% |
| forward | 3 | 92 | 5 | 0 | 0 | 0 | 0 | 100 | 92% |
| backward | 9 | 4 | 87 | 0 | 0 | 0 | 0 | 100 | 87% |
| LL | 1 | 2 | 0 | 74 | 0 | 15 | 8 | 100 | 74% |
| RL | 1 | 1 | 4 | 0 | 82 | 1 | 11 | 100 | 82% |
| LFOR | 0 | 0 | 0 | 5 | 1 | 90 | 4 | 100 | 90% |
| RFOL | 1 | 1 | 1 | 2 | 3 | 2 | 91 | 100 | 91% |
| total | 100 | 107 | 105 | 81 | 86 | 98 | 114 | | |
| precision | 85% | 86% | 83% | 91% | 95% | 92% | 80% | | |

An embodiment of the invention relates to a non-transitory computer-readable storage medium having computer code thereon for performing various computer-implemented operations. The term "computer-readable storage medium" is used herein to include any medium that is capable of storing or encoding a sequence of instructions or computer codes for performing the operations, methodologies, and techniques described herein. The media and computer code may be those specially designed and constructed for the purposes of the invention, or they may be of the kind well known and available to those having skill in the computer software arts. Examples of computer-readable storage media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits ("ASICs"), programmable logic devices ("PLDs"), and ROM and RAM devices. Examples of computer code include machine code, such as produced by a compiler, and files containing higher-level code that are executed by a computer using an interpreter or a compiler. For example, an embodiment of the invention may be implemented using Java, C++, or other object-oriented programming language and development tools. Additional examples of computer code include encrypted code and compressed code. Moreover, an embodiment of the invention may be downloaded as a computer program product, which may be transferred from a remote computer (e.g., a server computer) to a requesting computer (e.g., a client computer or a different server computer) via a transmission channel. Another embodiment of the invention may be implemented in hardwired circuitry in place of, or in combination with, machine-executable software instructions.

While the invention has been described with reference to the specific embodiments thereof, it should be understood by those skilled in the art that various changes may be made and equivalents may be substituted without departing from the true spirit and scope of the invention as defined by the appended claims. In addition, many modifications may be made to adapt a particular situation, material, composition of matter, method, operation or operations, to the objective, spirit and scope of the invention. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations is not a limitation of the invention.

What is claimed is:

1. A fabric-based pressure sensor array, comprising:
a continuous textile sheet having a first surface, a second surface opposite to the first surface, fibers coated with an electrically conductive material and disposed between the first surface and the second surface;

M elongated conductive strips directly coated on the first surface; and

N elongated conductive strips directly coated on the second surface, wherein the M elongated conductive strips extend crosswise relative to the N elongated conductive strips to define M×N intersections, wherein the continuous textile sheet has an offset resistivity corresponding to an initial offset pressure, and a variable resistivity in response to applied pressure so as to define M×N pressure sensors at locations corresponding to the M×N intersections, and the M elongated conductive strips and N elongated conductive strips are different from the fibers coated with the electrically conductive material, and wherein the sensor array is configured to detect a first pressure map corresponding to a first position of a body applying pressure to the continuous textile sheet, detect a second pressure map corresponding to a second position of the body applying pressure to the continuous textile sheet, and identify the second position of the body as being an identified one of a set of body positions based on output of a model using machine learning and receiving the first and second pressure maps as input.

2. The fabric-based pressure sensor array of claim 1, wherein the fibers are coated with an electrically conductive polymer.

3. The fabric-based pressure sensor array of claim 1, wherein the sensor array is configured to detect pressure applied at the M×N pressure sensors by an object positioned on the continuous textile sheet.

4. The fabric-based pressure sensor array of claim 1, wherein the fibers are woven to form the continuous textile sheet.

5. The fabric-based pressure sensor array of claim 1, wherein each of the M elongated conductive strips and the N elongated conductive strips includes an electrically conductive polymer.

6. The fabric-based pressure sensor array of claim 1, wherein each of the M elongated conductive strips and the N elongated conductive strips includes a polymer and electrically conductive additives dispersed in the polymer.

7. The fabric-based pressure sensor array of claim 1, wherein each of the M elongated conductive strips and the N elongated conductive strips includes a metal or a metal alloy.

8. The fabric-based pressure sensor array of claim 1, wherein M is greater than 1, N is greater than 1, and M is the same as N.

9. The fabric-based pressure sensor array of claim 1, wherein M is greater than 1, N is greater than 1, and M is different from N.

10. The fabric-based pressure sensor array of claim 1, wherein the fabric-based pressure sensor array has a thickness in a range of 0.1 mm to 1 mm.

11. The fabric-based pressure sensor array of claim 1, wherein the M×N pressure sensors are connected to a data sampling unit.

12. The fabric-based pressure sensor array of claim 1, wherein the set of body positions includes a situp position, a forward position, a backward position, a left lean position, a right lean position, a right foot over left position, and a left foot over right position.

13. The fabric-based pressure sensor array of claim 1, wherein one or more of the first and second positions of the body corresponds to a sleeping position.

* * * * *